(12) United States Patent
Son et al.

(10) Patent No.: US 11,158,093 B2
(45) Date of Patent: Oct. 26, 2021

(54) WORKSTATION, MEDICAL IMAGING DEVICE INCLUDING SAME, AND CONTROL METHOD THEREFOR

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Kihong Son, Yongin-si (KR); Jong Beom Ra, Yuseong-gu (KR); Seokhwan Jang, Yuseong-gu (KR); Kyoung-Yong Lee, Hwaseong-si (KR); Duhgoon Lee, Yongin-si (KR); Do Il Kim, Hwaseong-si (KR); Seungeon Kim, Namdong-gu (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/637,453

(22) PCT Filed: Aug. 6, 2018

(86) PCT No.: PCT/KR2018/008911
§ 371 (c)(1),
(2) Date: Feb. 7, 2020

(87) PCT Pub. No.: WO2019/031793
PCT Pub. Date: Feb. 14, 2019

(65) Prior Publication Data
US 2020/0250860 A1    Aug. 6, 2020

(30) Foreign Application Priority Data

Aug. 7, 2017  (KR) .......................... 10-2017-0099668
Jun. 25, 2018 (KR) .......................... 10-2018-0072716

(51) Int. Cl.
*G06T 11/00* (2006.01)
*A61B 6/00* (2006.01)
*G06T 7/20* (2017.01)

(52) U.S. Cl.
CPC ............ *G06T 11/005* (2013.01); *A61B 6/467* (2013.01); *A61B 6/5264* (2013.01); *A61B 6/54* (2013.01);
(Continued)

(58) Field of Classification Search
CPC ....... G06T 11/005; G06T 7/20; G06T 11/006; G06T 11/008; G06T 2207/10116;
(Continued)

(56) References Cited

U.S. PATENT DOCUMENTS

| | | |
|---|---|---|
| 6,330,298 B1 | 12/2001 | Tam |
| 10,321,886 B2 * | 6/2019 | Choi ..................... A61B 6/501 |
| 2007/0092055 A1 | 4/2007 | Vives et al. |

FOREIGN PATENT DOCUMENTS

| | | |
|---|---|---|
| JP | 2010-510833 | 4/2010 |
| KR | 10-2016-0087784 | 7/2016 |
| KR | 10-2017-0088742 | 8/2017 |

OTHER PUBLICATIONS

Extended European Search Report dated Mar. 23, 2020 from European Application No. 18843555.6, 7 pages.
(Continued)

*Primary Examiner* — Courtney D Thomas
(74) *Attorney, Agent, or Firm* — Staas & Halsey LLP

(57) ABSTRACT

A medical imaging apparatus includes an X-ray source configured to irradiate X-rays to an object; an X-ray detector
(Continued)

configured to detect the X-rays radiated from the X-ray source to obtain projection data; and an image processor configured to reconstruct the projection data based on a motion parameter representing movement of at least one of the object, the X-ray source, and the X-ray detector, and to generate a medical image by applying a weighting process to the reconstructed projection data.

15 Claims, 20 Drawing Sheets

(52) U.S. Cl.
CPC .............. *G06T 7/20* (2013.01); *G06T 11/006* (2013.01); *G06T 11/008* (2013.01); *A61B 6/4078* (2013.01); *A61B 6/4085* (2013.01); *G06T 2207/10116* (2013.01); *G06T 2207/30168* (2013.01); *G06T 2211/421* (2013.01)

(58) Field of Classification Search
CPC ..... G06T 2207/30168; G06T 2211/421; G06T 2211/412; A61B 6/467; A61B 6/5264; A61B 6/54; A61B 6/4078; A61B 6/4085; A61B 6/032
See application file for complete search history.

(56) References Cited

OTHER PUBLICATIONS

Jang et al.: "Motion compensated reconstruction for 3D head motion", the 4th International Conference on Image Formation in X-RAY Computed Tomography, Jul. 18, 2016, pp. 519-522.
European Office Action dated Oct. 8, 2020 from European Application No. 18843555.6, 5 pages.
European Office Action dated May 20, 2021 from European Application No. 18843555.6, 4 pages.

* cited by examiner (a) (b) (c)

WORKSTATION, MEDICAL IMAGING DEVICE INCLUDING SAME, AND CONTROL METHOD THEREFOR

CROSS-REFERENCE TO RELATED APPLICATIONS

This application is a U.S. National Stage Application which claims the benefit under 35 U.S.C. § 371 of International Patent Application No. PCT/KR2018/008911 filed on Aug. 6, 2018, which claims foreign priority benefit under 35 U.S.C. § 119 of Korean Patent Application No. 10-2017-0099668 filed on Aug. 7, 2017 and Application No. 10-2018-0072716 filed on Jun. 25, 2018, in the Korean Intellectual Property Office, the contents of all of which are incorporated herein by reference.

TECHNICAL FIELD

The present disclosure relates to a workstation for obtaining an improved image quality with reduced motion artifacts, a medical imaging apparatus including the same and a method of controlling the workstation.

BACKGROUND ART

A medical imaging apparatus is an apparatus that portrays images of interiors of target objects for diagnostic or therapeutic purposes, and includes apparatuses with varieties of modalities, such as a magnetic resonance imaging (MRI) apparatus, a radiography apparatus, a mammography apparatus, a positron emission tomography (PET) apparatus, a computed tomography (CT) apparatus, a single photon emission computed tomography (SPECT) apparatus, an optical coherence tomography (OCT) apparatus, and the like.

Particularly, the medical imaging apparatus captures and processes structural details, internal tissue, and fluid flow within a body and presents them to a user. The user such as a doctor may diagnose a health condition and a disease of a patient by using a medical image outputted from the medical imaging apparatus. As the accuracy of the medical image increases, the patient's condition may be more accurately determined.

Recently, a study is being conducted on a method for more accurately obtaining the medical image.

DISCLOSURE

Technical Problem

The present invention provides a workstation that generates a medical image reconstructed through rebinning based on a motion of an object, thereby minimizing artifacts caused by the motion of the object and obtaining an improved medical image, a medical imaging apparatus including the same and a method of controlling the workstation.

Technical Solution

An aspect of the disclosure provides a medical imaging apparatus including: an X-ray source configured to irradiate X-rays to an object; an X-ray detector configured to detect the X-rays radiated from the X-ray source to obtain projection data; and an image processor configured to reconstruct the projection data based on a motion parameter representing movement of at least one of the object, the X-ray source, and the X-ray detector, and to generate a medical image by applying a weighting process to the reconstructed projection data.

The image processor may be configured to generate a local weight function based on the motion parameter, and to apply the weighting process including the local weight function to the reconstructed projection data.

The image processor may be configured to apply an image quality metric process to determine the motion parameter.

The image processor may be configured to determine the motion parameter by adjusting the reconstructed image based on the projection data.

The image processor may be configured to reconstruct the projection data based on rebinning converting the projection data.

The image processor may be configured to apply the weighting process based on the reconstructed projection data applying a filtering process.

The image processor may be configured to apply the weighting process by combining the local weight function and a preset global weight function.

The rebinning may be configured to convert projection data of fan-beam or cone-beam geometry into projection data of parallel-beam geometry.

The filtering process may be configured to apply a ramp filtering process after executing data padding to fill preset projection data.

Another aspect of the disclosure provides a workstation including: an interface configured to receive a scan command about an object from a user; a controller configured to control an X-ray source for irradiating X-rays according to the received scan command and an X-ray detector for detecting the irradiated X-rays to obtain projection data; and an image processor configured to reconstruct the projection data based on a motion parameter representing movement of at least one of the object, the X-ray source, and the X-ray detector, and to generate a medical image by applying a weighting process to the reconstructed projection data.

The image processor may be configured to generate a local weight function based on the motion parameter, and to apply the weighting process including the local weight function to the reconstructed projection data.

The controller may be configured to transmit raw data obtained based on at least one of the scan command, the X-ray source, and the X-ray detector to the image processor. The image processor may be configured to preprocess the raw data to obtain the projection data.

The image processor may be configured to generate a sinogram based on the projection data, and to reconstruct the projection data based on the sinogram.

The image processor may be configured to apply the weighting process by combining the local weight function and a preset global weight function.

Another aspect of the disclosure provides a method of controlling a workstation including: receiving, by an interface, a scan command about an object from a user; controlling, by a controller, an X-ray source for irradiating X-rays according to the received scan command and an X-ray detector for detecting the irradiated X-rays to obtain projection data; and generating, by an image processor, a medical image based on a motion parameter representing movement of at least one of the object, the X-ray source, and the X-ray detector.

Advantageous Effects

According to the above-described workstation, the medical imaging apparatus including the same and the method of controlling the workstation, by generating the medical image reconstructed through rebinning based on a motion of the object, it is possible to minimize artifacts caused by the motion of the object and obtain an improved medical image.

MODES OF THE INVENTION

Figure 1A:
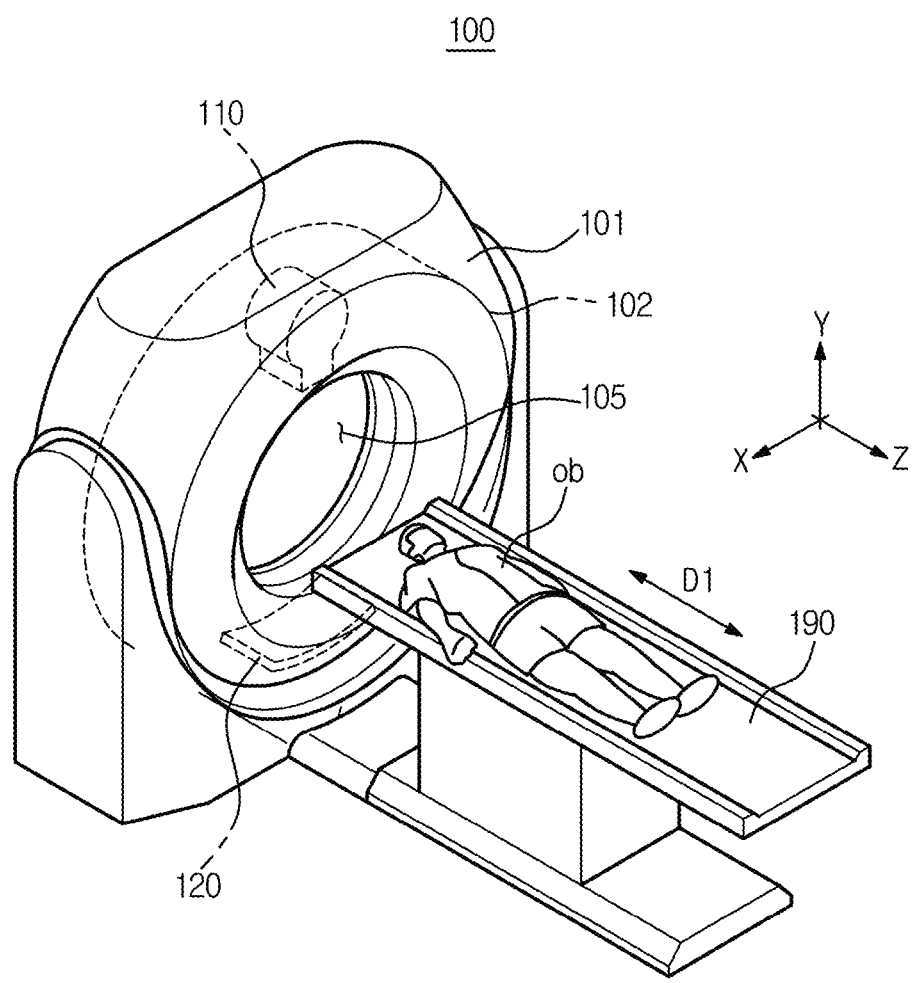
FIGS. 1A and 1B are views illustrating an appearance of a medical imaging apparatus as an example of the medical imaging apparatus.

To clarify the scope of the present disclosure and enable one having ordinary skill in the art to which the present disclosure pertains to practice the present disclosure, the principles of the present disclosure are described and exemplary embodiments thereof are disclosed herein. The disclosed exemplary embodiments may be implemented in various forms.

Like reference numerals refer to like elements throughout the specification. Not all elements of exemplary embodiments of the disclosure will be described, and description of what are commonly known in the art or what overlap each other in the embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

The image herein may include a medical image acquired by a medical imaging apparatus, such as a magnetic resonance imaging (MRI) apparatus, a computed tomography (CT) apparatus, an ultrasound imaging device, or an x-ray imaging device.

An "object" herein refers to the object to be captured and may include a human being, an animal, or a part thereof. For example, the object may include a part of a body (an organ), a phantom, or the like.

The medical imaging apparatus refers to an apparatus that obtains the medical image by imaging the inside of the object. Here, an object ob may be a living body of a human or animal, or an in vivo tissue such as vessels, bones, muscles, or the like, but is not limited thereto. Any object may be applied as long as its internal structure can be imaged by a variety of signals irradiated by the medical imaging apparatus.

The medical imaging apparatus, which will be described below, includes all types of apparatuses that obtain medical images obtained by imaging the inside of the object. For example, the medical imaging apparatus includes all apparatuses capable of obtaining the medical image of the inside of the object, such as a magnetic resonance imaging (MRI) apparatus and an ultrasound imaging apparatus using an ultrasound probe. In addition, the medical imaging apparatus includes all tomography apparatuses such as a computed tomography (CT) imaging apparatus, an optical coherence tomography (OCT) apparatus, and a positron emission tomography (PET)-CT imaging apparatus.

Hereinafter, as an example of the medical imaging apparatus, the CT imaging apparatus will be described as an example. However, embodiments to be described below are not limited thereto, and any apparatus capable of obtaining the medical image may be applied.

Hereinafter, embodiments of the present disclosure will be described in detail with reference to the accompanying drawings.

Figure 1B:
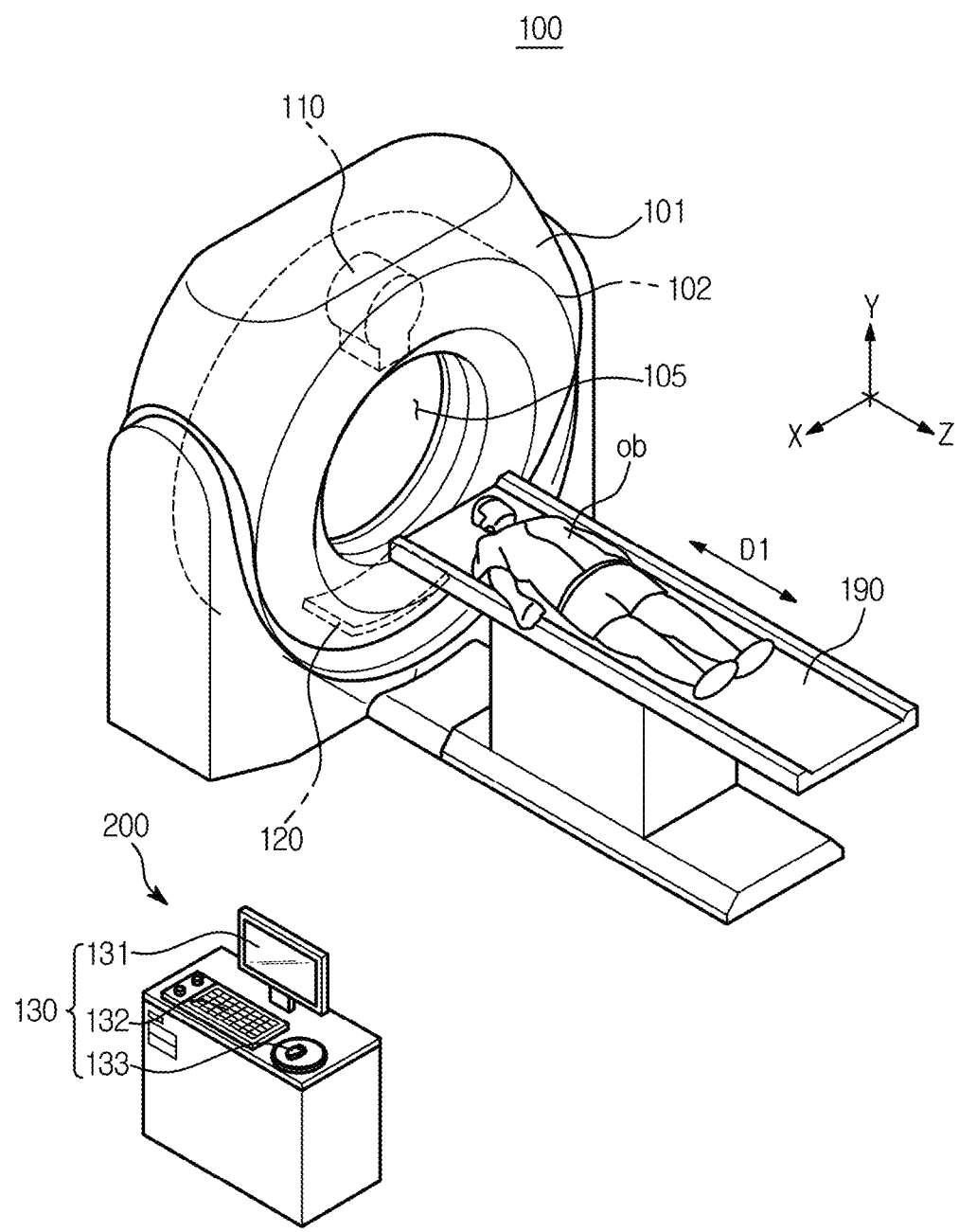
Figure 2:
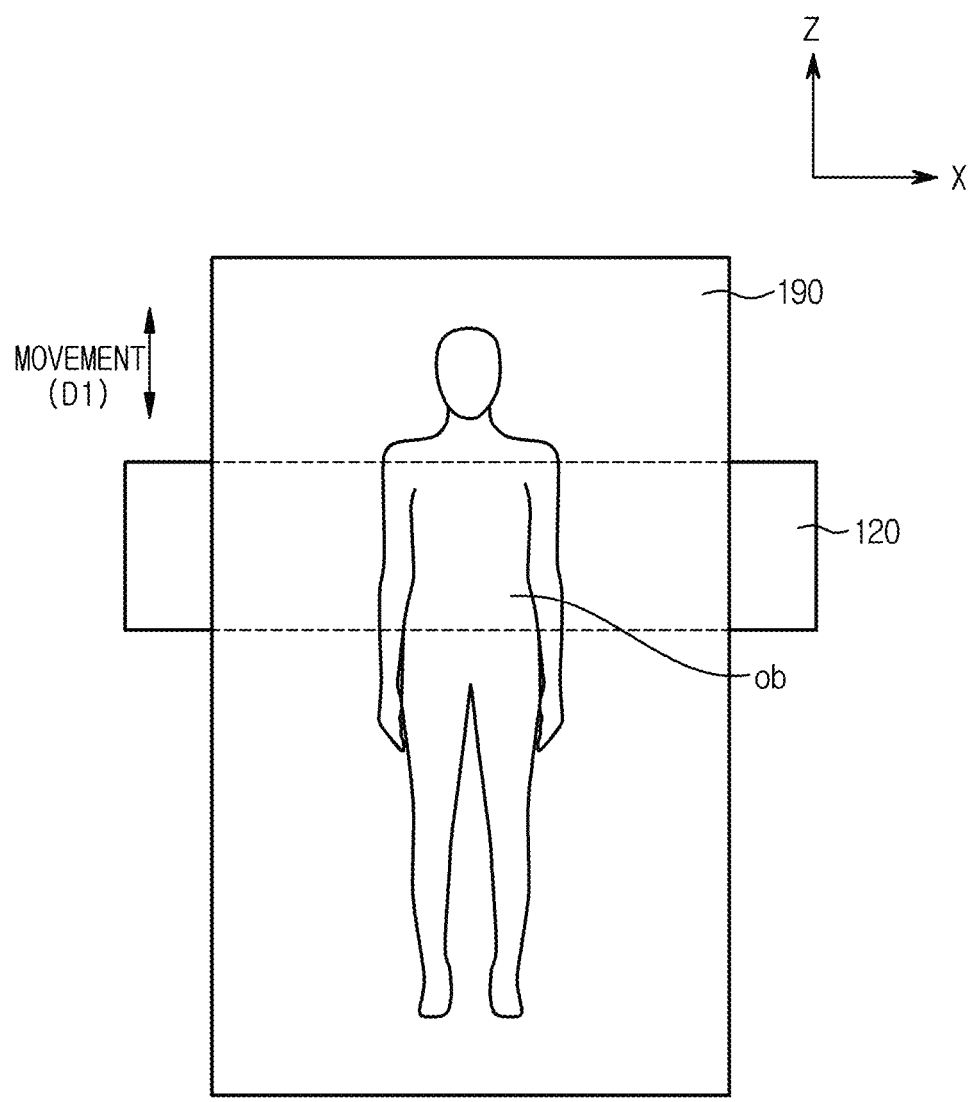
FIG. 2 is a view illustrating a table on which an object is placed according to an embodiment.
Figure 3:
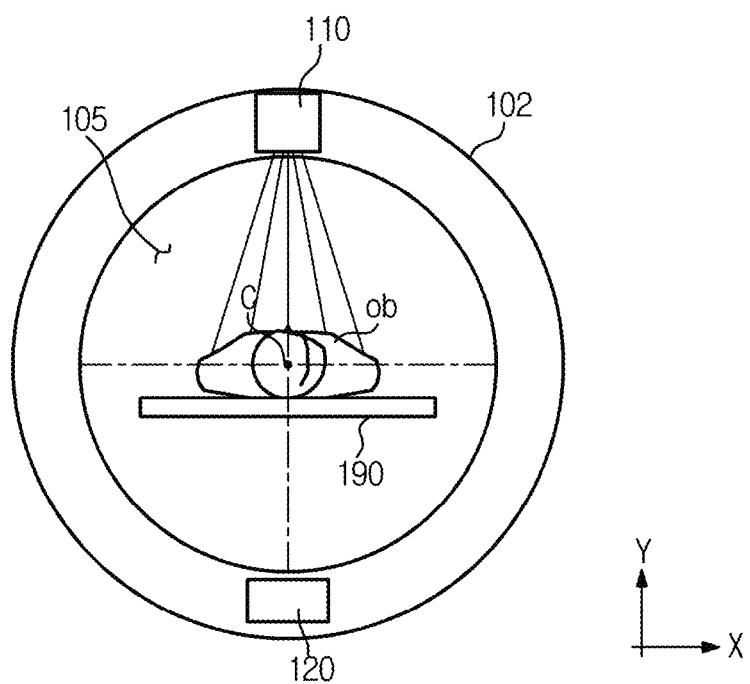
FIGS. 3 and 4 are views illustrating a relationship between an X-ray source and an X-ray detector and an object located between the X-ray source and the X-ray detector according to different embodiments.
Figure 4:
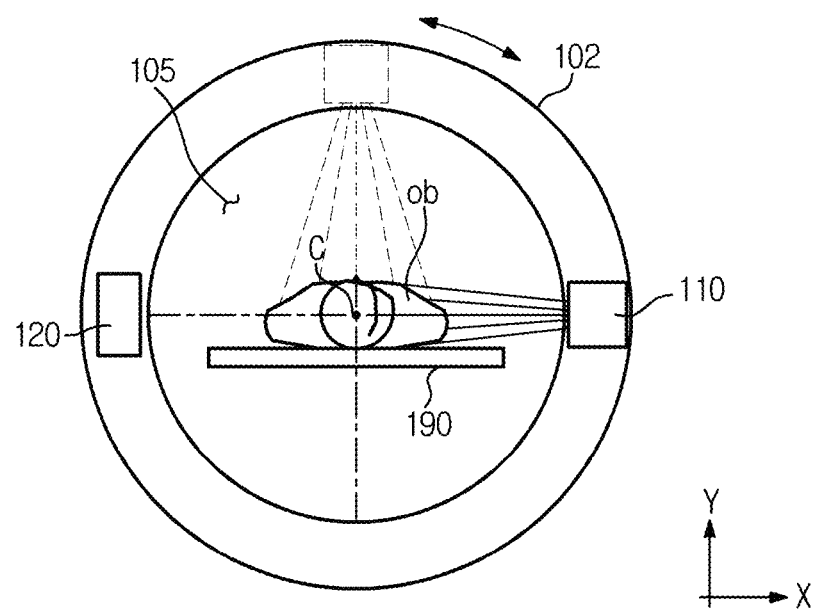
Figure 5:
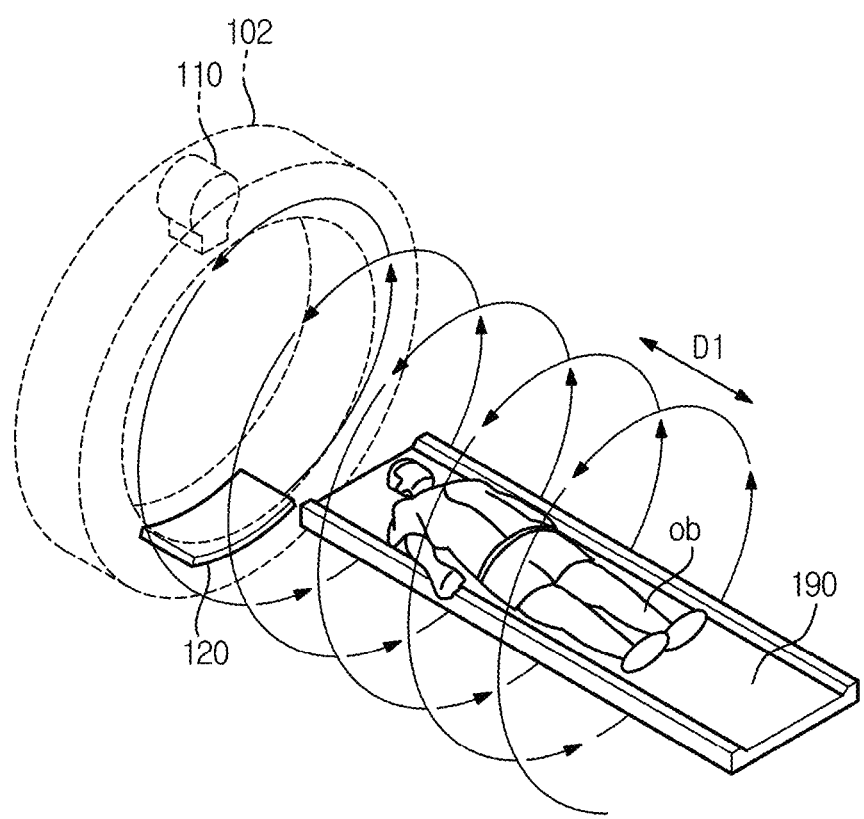
FIG. 5 is a view illustrating a case where a scan is performed through a helical scan method according to an embodiment.
Figure 6A:
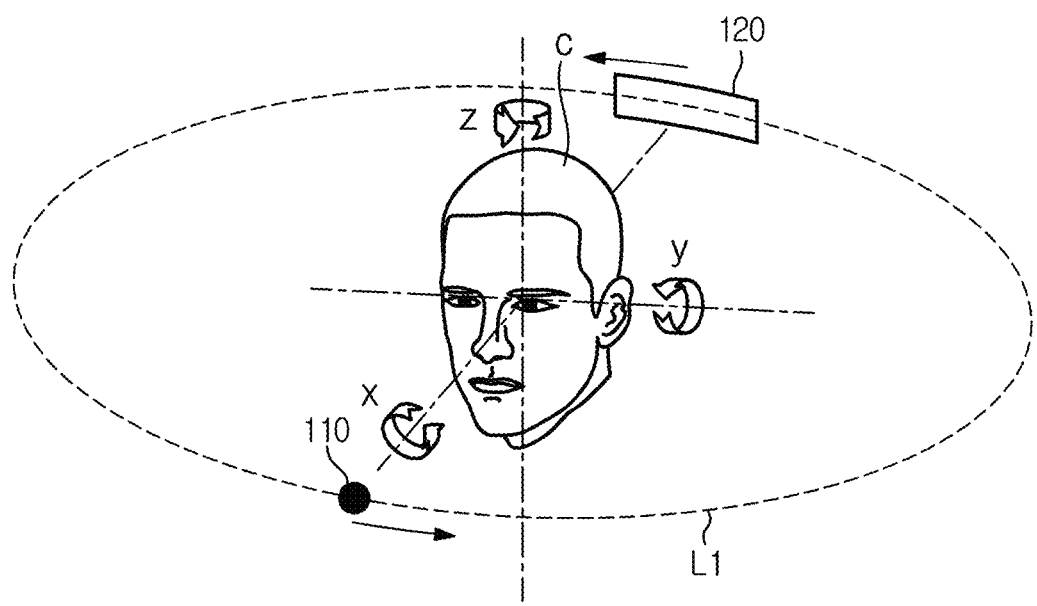
FIGS. 6A and 6B are views illustrating trajectories of rotation of X-ray sources according to different embodiments.
Figure 6B:
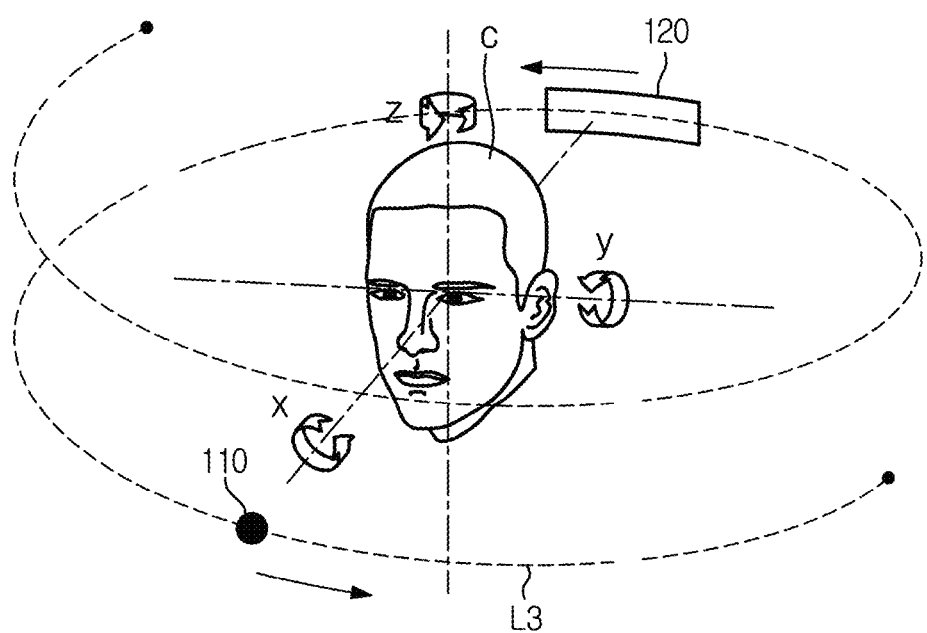

FIGS. 1A and 1B are views illustrating an appearance of a medical imaging apparatus as an example of the medical imaging apparatus, FIG. 2 is a view illustrating a table on which an object is placed according to an embodiment, FIGS. 3 and 4 are views illustrating a relationship between an X-ray source and an X-ray detector and an object located between the X-ray source and the X-ray detector according to different embodiments, FIG. 5 is a view illustrating a case where a scan is performed through a helical scan method according to an embodiment, and FIGS. 6A and 6B are views illustrating trajectories of rotation of X-ray sources according to different embodiments. The embodiment will be described in connection with FIGS. 1A to 6B together to avoid overlapping explanation.

Referring to FIG. 1A, a medical imaging apparatus 100 may include a housing 101 on which irradiation and detection of X-rays is performed, and a table 190 for moving an object ob.

A cylindrical gantry 102 may be provided inside the housing 101. Inside the gantry 102, an X-ray source 110 for irradiating X-rays and an X-ray detector 120 for detecting X-rays may be provided to face each other.

The object ob may be located between the X-ray source 110 and the X-ray detector 120. In this case, the object ob may be located on the table 190, and the table 190 may enter the inside of the gantry 102 (a D1 direction).

Referring to FIG. 1B, the medical imaging apparatus 100 may include a workstation 200 that performs operation control and image restoration of the medical imaging apparatus 100. Here, the workstation 200 may also be referred to as a host apparatus or a console. Hereinafter, for convenience of description, an apparatus for controlling the overall operations of the medical imaging apparatus 100 will be referred to as the workstation 200. A detailed description of the workstation 200 will be described later.

Referring to FIG. 2, the object ob is transmitted into the gantry 102 while lying on the table 190, and when a scan portion of the object ob, that is, a region of interest (ROI), is located in a scan position, the X-ray source and the X-ray detector inside the gantry 102 irradiate and detect X-rays while rotating, thereby scanning the object ob. Thus, the medical imaging apparatus 100 may obtain the medical image based on the scan result.

Figure 7A:
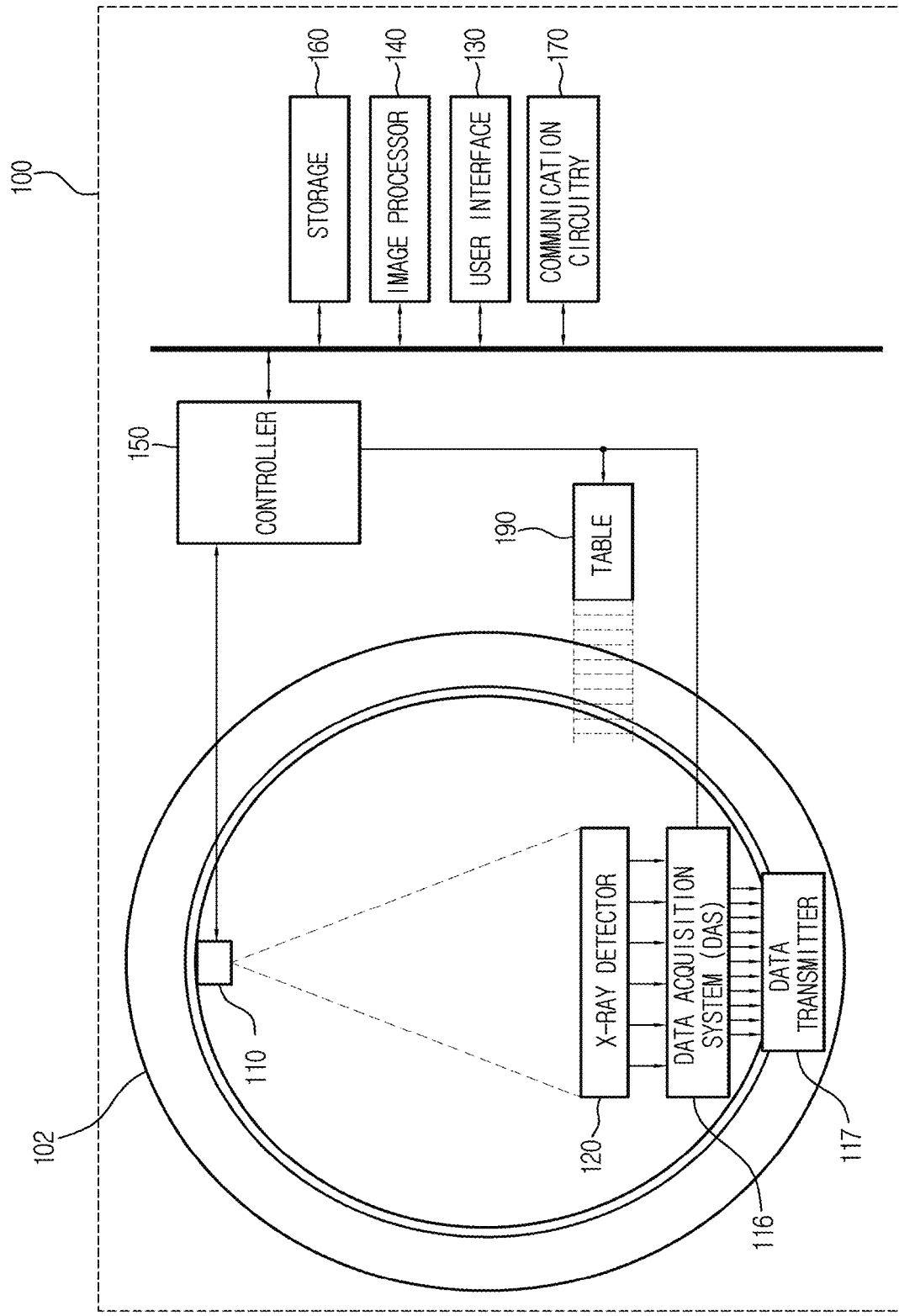
FIGS. 7A and 7B are control block diagrams of a medical imaging apparatus according to different embodiments.

The gantry 102 may include a rotating frame, the X-ray source 110, the X-ray detector 120, a data acquisition system 116 (see FIG. 7A), and a data transmitter 117 (see FIG. 7A).

The X-ray source 110 may refer to a device that generates X-rays and irradiates the object ob. The X-ray source 110 may further include a filter for filtering X-rays to be irradiated.

The X-ray source 110 may radiate X-rays in various forms. For example, the X-ray source 110 may radiate X-rays in the form of a three-dimensional (3D) cone-beam or radiate X-rays in the form of a two-dimensional (2D) fan-beam.

The X-ray detector 120 is a device for detecting X-rays transmitted through the object ob.

When the table 190 enters into the gantry 102, the object ob may be located between the X-ray source 110 and the X-ray detector 120. In this case, X-rays radiated from the X-ray source 110 may be transmitted through the object ob and detected by the X-ray detector 120.

The X-ray detector 120 mat detect X-rays radiated from the X-ray source 110 and generate an electric signal corresponding to an intensity of the detected X-rays.

The X-ray detector 120 may be implemented in various forms. For example, the X-ray detector 120 may be implemented in a flat form or in a curved form.

Meanwhile, a detailed description of the data acquisition system 116 and the data transmitter 117 will be described later.

Referring to FIGS. 3 and 4, the X-ray source 110 and the X-ray detector 120 may be provided to be opposite to each other. The X-ray source 110 and the X-ray detector 120 may obtain raw data by performing the irradiation and detection of X-rays while rotating at 360° through the rotating frame.

Here, the raw data may refer to the converted electrical signal after the X-ray detector 120 detects the X-rays detected by passing through the object ob, and may refer to data before a pre-processing process or the like is performed. A detailed description thereof will be described later.

When a head c of the object ob is to be scanned according to an embodiment, as illustrated in FIGS. 3 and 4, the X-ray source 110 and the X-ray detector 120 may obtain the raw data through the irradiation and detection of X-rays while rotating at 360° about the head c.

The object ob is transmitted into the gantry 102 while lying on the table 190, and when the scan portion of the object ob, that is, the ROI, is located in the scan position, the X-ray source and the X-ray detector irradiate and detect X-rays while rotating, thereby scanning the object ob.

The scan of the object ob may be performed in a state where the table 190 is fixed, for example, in an axial scan method.

In an embodiment, when the table 190 on which the object ob lies is transmitted to the inside of the gantry 102 at a constant speed, the scan portion of the object ob, that is, the ROI, may be located at the scan position. Then, the table 190 stops and the X-ray source 110 and the X-ray detector 120 inside the gantry 102 may rotate to scan and detect X-rays to scan the object ob.

In addition, the scanning method of the object ob is not limited to the above-described example. For example, the scan of the object ob may be performed in a state in which the table 190 moves in a specific axial direction as a helical scan method, or may be performed as the X-ray source 110 and the X-ray detector 120 rotate while moving in the specific axial direction in a state in which the table 190 is fixed.

Referring to FIG. 5, any one of the gantry 102 or the table 190 equipped with the X-ray source 110 and the X-ray detector 120 may move in a D1-axis direction during scanning.

For example, while the X-ray source 110 and the X-ray detector 120 rotate, the table 190 may move at a constant speed in the D1-axis direction. In this case, the scan of the object ob may be performed by irradiating and detecting X-rays while the X-ray source 110 and the X-ray detector 120 rotate. As the scan is performed while the table 190 is moved, the X-ray source 110 and the X-ray detector 120 may scan while rotating the object ob in a helical manner as illustrated in FIG. 5.

Referring to FIG. 6A, the medical imaging apparatus 100 may obtain a medical image of the head c of the object by radiating X-rays to the head c of the object through the X-ray source 110. The X-ray source 110 and the X-ray detector 120 rotate 360° along a trajectory L1 while facing each other, and may obtain the raw data at various views, that is, at various scan points or scan angles.

Referring to FIG. 6B, the medical imaging apparatus 100 may obtain the medical image of the head c of the object ob by rotating the X-ray source 110 in the helical manner and radiating X-rays to the head c of the object ob. The X-ray source 110 and the X-ray detector 120 may obtain raw data at various scan points or scan angles while rotating according to a trajectory L3.

Meanwhile, the object ob or the head c may move while the object ob or the head c of the object ob is scanned by the above-described scanning method. In addition, as illustrated in FIG. 5, while the table 190 moves inside the gantry 102, the table 190 may shake or the object ob may move.

For example, when a bottom surface on which the medical imaging apparatus 100 is located is not flat, the medical imaging apparatus 100 such as the table 190 or the gantry 102 may be moved during movement.

As another example, when the medical imaging apparatus 100 is a mobile CT apparatus mainly used in an operating room or the like, a motion may be generated by various factors.

During the scan, the motion may be generated in the X-ray source 110, the X-ray detector 120, and the object ob. Due to the motion, not only a distance between the X-ray source 110 and the X-ray detector 120, but also a distance between the X-ray source 110 and the object ob, and a distance between the X-ray detector 120 and the object ob may change, and may cause artifacts in the generated medical image.

The medical imaging apparatus 100 according to an embodiment may improve image quality deterioration due to the artifacts by processing the raw data based on the motion. A detailed description thereof will be described later with reference to the accompanying drawings.

Figure 7B:
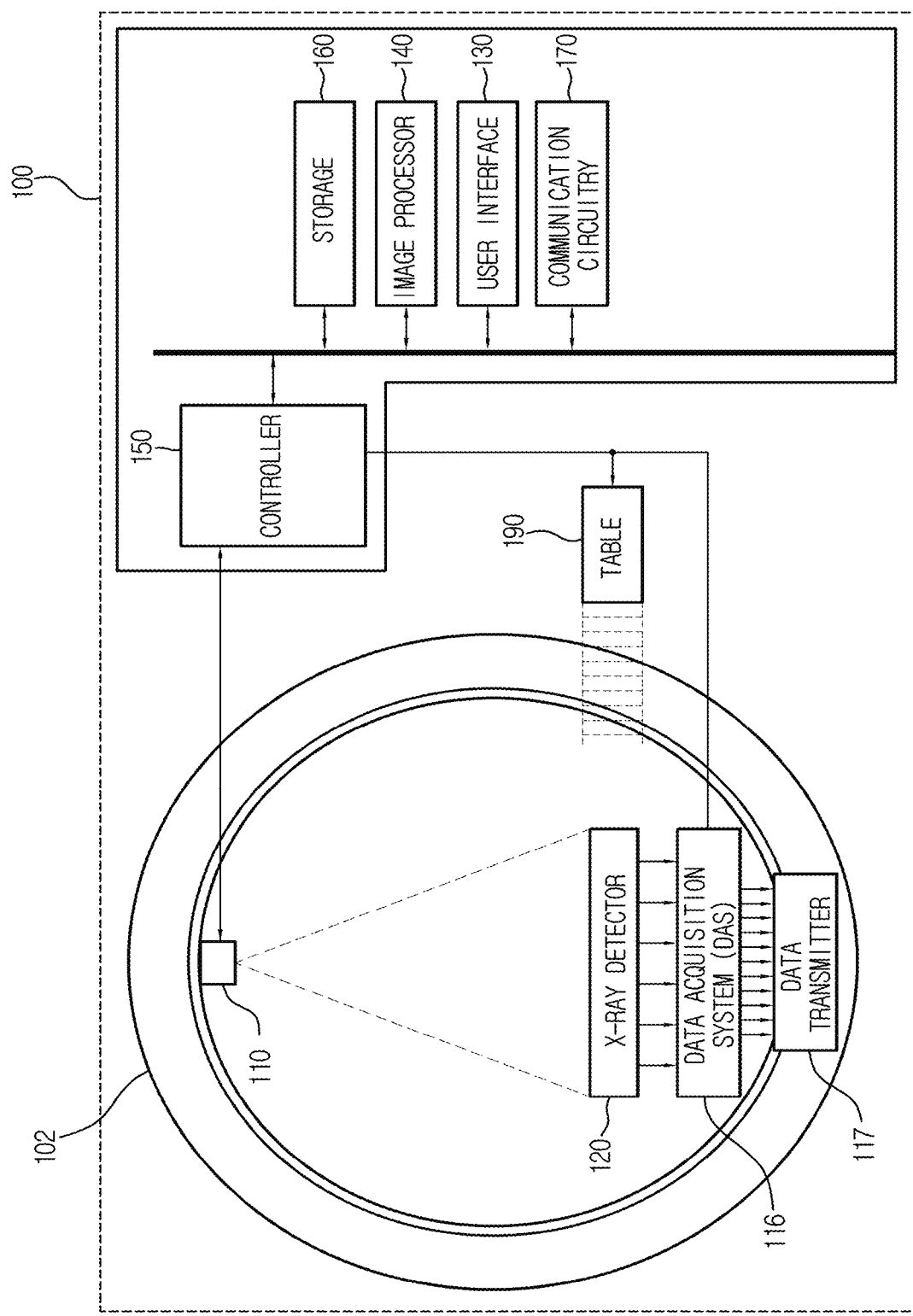

FIGS. 7A and 7B are control block diagrams of a medical imaging apparatus according to different embodiments.

Referring to FIG. 7A, the medical imaging apparatus 100 may include the gantry 102, the X-ray source 110, the data acquisition system 116, the data transmitter 117, the X-ray detector 120, a user interface 130, an image processor 140, a controller 150, a storage 160, a communication circuitry 170, and the table 190.

Here, at least one of the image processor 140, the controller 150, the storage 160, and the communication circuitry 170 may be integrated in a system on chip (SOC) embedded in the medical imaging apparatus 100. However, a plurality of the SOCs rather than one of the SOCs, which is embedded in the medical imaging apparatus 100, may be present, and therefore the present disclosure is not limited to a case in which the at least one of the image processor 140, the controller 150, the storage 160, and the communication circuitry 170 may be integrated in only one of the SOCs.

Since the description of the X-ray source 110, the X-ray detector 120, and the table 190 has been described above, a detailed description thereof will be omitted.

The table 190 is movable in a predetermined direction (e.g., at least one of an x-axis direction, a y-axis direction, and a z-axis direction). Meanwhile, the movement of the table 190 may be controlled through a control signal of the controller 150.

The data acquisition system (DAS) 116 may be connected to the X-ray detector 120 by wire or wirelessly to collect digital signals generated from the X-ray detector 120, that is, digital data. Here, the digital data may be transmitted to the image processor 140 by wire or wirelessly through the data transmitter 117. Here, the transmitted digital data is raw data.

The user interface 130 may receive various control commands related to the operation of the medical imaging apparatus 100 from a user and provide various information.

Particularly, the user interface 130 may receive the user's command or output the medical image generated by the image processor 140 through a display. In addition, the user interface 130 may generate or change the number and interval of control points for determining a motion parameter, which will be described later, and may change various setting values included in the medical imaging apparatus 100.

The image processor 140 may perform various processes for obtaining the medical image. The image processor 140 may be implemented through a graphics processor and a graphics memory.

The image processor 140 may receive the raw data and perform the pre-processing process. Here, the pre-processing process is a necessary process for obtaining projection data, and may include a variety of processes necessary for obtaining the projection data, such as a process for correcting unevenness of sensitivity between channels, a sharp decrease in signal strength, or a process for correcting loss of a signal due to an X-ray absorber such as a metal.

The projection data may refer to a set of row data obtained at one scan angle, and the set of row data obtained through the above-described scanning method is referred to as the projection data.

The image processor 140 may generate a sinogram by obtaining projection data at all scan angles. That is, the projection data means a set of the raw data collected through the same scan angle for all channels.

The image processor 140 may generate the medical image by applying a reconstruction technique, which will be described later, in the collected sinogram after the X-ray source 110 irradiates a fan-beam or cone-beam having a constant angle. A detailed description thereof will be described later with reference to FIG. 8.

As described above, the object ob may move during X-ray irradiation, that is, during scanning. For example, the head c of the user may be moved during the scan. Accordingly, the image processor 140 may minimize artifacts by simultaneously applying a technique for processing an image and simultaneously correcting the motion of the object ob.

In detail, the image processor 140 may apply a reconstruction process by reflecting a motion parameter including the motion of the object ob in generating the medical image from the obtained sinogram.

Here, the motion parameter may refer to a parameter that can represent a degree of motion of the object ob through a coordinate system. The coordinate system may include all kinds of coordinate systems that can represent the coordinate of the motion of the object ob.

For example, when using a rectangular coordinate system that represents coordinates in three orthogonal axes (x-axis, y-axis, and z-axis), the motion parameter may be represented as an angle and a distance to the x-axis, y-axis, and z-axis of the object ob.

In this case, the motion parameter may be composed of six parameters Rx ($\Psi$), Ry ($\Phi$) Rz ($\theta$), Tx, Ty, and Tz. Here, the Rx ($\Psi$) may represent the angle of rotation of the object ob about the x-axis, the Ry $\Phi$) may represent the angle of rotation of the object ob about the y-axis, and the Rz ($\theta$) may represent the angle of rotation of the object ob about the z-axis. In addition, the Tx may represent the distance the object moved along the x-axis, the Ty may represent the distance the object moved along the y-axis, and the Tz may represent the distance the object moved along the z-axis.

The motion parameter may include the motion of the components of the medical imaging apparatus 100 as well as the motion of the object ob itself. The medical imaging apparatus 100 may reconstruct the image by reflecting not only the motion of the object but also the motion parameter reflecting motions of the components of the medical imaging apparatus 100.

For example, when the motion is generated in the object ob at a specific scan time or scan point, it is assumed that the object ob has no motion. When the motion of the object ob is reflected by the motion of the X-ray source 110 and the X-ray detector 120, the motion of the object ob may be reflected on a virtual trajectory.

In other words, when the motion of the object ob is generated at the specific scan time or scan point, the motion of the object ob may be relatively reflected as the motion of the component in the medical imaging apparatus 100.

For example, when the object ob is moved by +1 cm on the x-axis, if the X-ray source 110 and the X-ray detector 120 are reflected and moved by −1 cm on the x-axis, the movement of the object ob may be reflected. Accordingly, when the position of the X-ray source 110 and the X-ray detector 120 is moved by −1 cm on the x-axis on the virtual trajectory to compensate for the motion of the object ob, the motion of the object ob on the virtual trajectory may be reflected.

When the X-ray source 110 and the X-ray detector 120 are moved by +1 cm on the x-axis, if the object ob is reflected and moved by −1 cm on the x-axis, the movement of the X-ray source 110 and the X-ray detector 120 may be reflected. Accordingly, when the position of the X-ray source 110 and the X-ray detector 120 is moved by +1 cm on the x-axis on the virtual trajectory to compensate for the motion of the object ob, the motion of the X-ray source 110 and the X-ray detector 120 on the virtual trajectory may be reflected.

Meanwhile, the motion parameter may further include a parameter Tsd representing the motion between the X-ray source 110 and the X-ray detector 120 in addition to the six parameters described above.

The image processor 140 may determine the motion of the object ob, the X-ray source 110, and the X-ray detector 120 through the above-described motion parameter.

The method of determining the motion parameter may vary. For example, the medical imaging apparatus 100 may determine a motion parameter by a reconstructed medical image from the projection data.

In detail, the image processor 140 may determine the motion parameter based on an initial value stored in graphics memory, and then generate a first medical image. In addition, the image processor 140 may adjust a motion parameter value updated through the reconstruction technique, and may determine the motion parameter value when the medical image is neatly presented as the motion parameter value representing the motion of the object ob at a corresponding scan time or scan point.

That is, the image processor 140 may evaluate the image quality while adjusting the motion parameter value for the reconstructed first medical image, and may determine an optimal motion parameter value based on the evaluation result, and may determine this as the motion parameter.

As another example, the image processor 140 may apply an image quality metric process to determine a scan parameter or the motion parameter value at the corresponding scan time or scan point based on the result value.

Here, the image quality metric process may refer to one of quantitative techniques for determining the image quality.

The image processor 140 may apply the image quality metric process to determine a value when the result value is the smallest as the motion parameter value at the corresponding scan time or scan point.

Meanwhile, a detailed description of determining the motion parameter will be described later with reference to FIG. 8.

The medical imaging apparatus 100 may be provided with the controller 150. The controller 150 may be implemented through an operation processing device such as a processor, and may control the overall operations of the medical imaging apparatus 100. In detail, the controller 150 may generate the control signal for controlling the components of the medical imaging apparatus 100 to control the operations of each of the components of the medical imaging apparatus 100.

For example, the controller 150 may control the operations of the X-ray source 110 and the X-ray detector 120 based on the control command input from the user interface 130 to obtain the raw data at various angles. As another example, the controller 150 may control the data acquisition system 116 through the control signal so that the raw data obtained by the X-ray detector 120 may be transmitted to the image processor 140.

In addition, the controller 150 may control the operation of the table 190 to allow the object ob to enter the gantry 102, and may provide the medical image obtained to the user through the user interface 130.

The medical imaging apparatus 100 may be provided with the storage 160 that stores various data related to a method of controlling the operation of the medical imaging apparatus 100.

In detail, the storage 160 may store the initial values of the motion parameters, the determined motion parameters, and the like. In addition, the storage 160 may store the medical image generated by the image processor 140 as well as a program required for the operation of the controller 150.

The storage 160 may be implemented through at least one type of memory among a flash memory type memory, a hard disk type memory, a multimedia card micro type memory, a card type memory (e.g., SD or XD memory, etc.), RAM (random access memory), SRAM (static random access memory), ROM (read-only memory), EEPROM (electrically erasable programmable read-only memory), PROM (programmable read-only memory), a magnetic memory, a magnetic disk, and an optical disk. However, the storage 160 is not limited thereto, and it may be implemented in any other form known in the art.

Meanwhile, the controller 150 and the storage 160 may be implemented as separate chips, but the controller 150 and the storage 160 may be integrated with a single chip.

The communication circuitry 170 may be provided in the medical imaging apparatus 100.

The communication circuitry 170 may include at least one of a wired communication module and a wireless communication module. Accordingly, the communication circuitry 170 may exchange data with an external device through at least one of a wired communication network and a wireless communication network. The wired communication module and the wireless communication module may be implemented as separate chips, or may be integrated into a single chip.

As an example, the communication circuitry 170 may exchange data with a hospital server or another medical apparatus in a hospital connected through a Picture Archiving and Communication System (PACS) through the wired/wireless communication network, and may exchange data according to Digital Imaging and Communications in Medicine (DICOM) standards.

The communication circuitry 170 may support sharing of data related to diagnosis of the object ob and the medical image generated by another one of the medical imaging apparatuses 100 through a wired/wireless communication method, thereby enabling a doctor to make an integrated diagnosis on the object ob.

The communication circuitry 170 may receive a diagnosis history or a treatment schedule of a patient from a server and use the same to diagnose the object ob. The communication circuitry 170 may perform data communication with an electronic device of the doctor or a customer, as well as a server or a medical apparatus in the hospital.

The communication circuitry 170 may transmit the wired/wireless communication network to the user with quality information regarding an abnormality of the medical apparatus or the medical image, and may receive feedback from the user.

Referring to FIG. 7B, at least one of the components of the medical imaging apparatus 100 may be included in the workstation 200. For example, the user interface 130, the image processor 140, the controller 150, the storage 160, and the communication circuitry 170 may be included in the workstation 200. The workstation 200 and the components of the medical imaging apparatus 100 that are not included in the workstation 200, such as the X-ray source 110, the X-ray detector 120, etc. may be connected wirelessly or wired, and may transmit and receive various commands, data, and the like.

The housing 101 including the workstation 200 and the components for scanning the object ob may be provided together in a capturing room. Alternatively, the capturing room in which the object ob is scanned and a control room controlling capturing and image processing operations of the object ob may be separated. In this case, the housing 101 including the components for scanning the object ob may be provided in the capturing room, and the workstation 200 may be provided in a scanning room.

Referring to FIG. 1B, the workstation 200 may be provided with the user interface 130 for user manipulation.

The user interface 130 may receive instructions or commands for controlling the operations of the medical imaging apparatus 100 from the user, and may provide various screens related to the operations of the medical imaging apparatus 100.

In one embodiment, the user interface 130 may be implemented through a display 131 that provides various information to the user visually, a keyboard 132 that receives various control commands from the user, and a mouse 133.

The user interface 130 may be implemented through a physical configuration such as a trackball, a foot switch, and a foot pedal, and may include various devices capable of interacting with the user.

In addition, although the user interface 130 may be provided on an upper portion of the workstation 200 as illustrated in FIG. 1B, it may be provided at a lower portion when the user interface 130 is implemented as the foot switch and the foot pedal as described above.

On the other hand, the user interface 130 may display a graphical user interface (GUI) on the display 131 which is implemented graphically so that an operation of exchanging various information and commands between the user and the medical imaging apparatus 100 is performed more conveniently, thereby enabling interaction between the user and the medical imaging apparatus 100. In this case, the user interface 130 may be implemented by only the display 131.

The user interface 130 may input the control command regarding the operations of the medical imaging apparatus 100, such as a command for moving the table 190 in which the object ob is located, a command for selecting an X-ray capturing mode, a command for X-ray capturing conditions, a command for displaying a captured image, and the like. In addition, the user may select an X-ray capturing start command, select a type of capturing, and set the ROI through the user interface 130, and there is no limitation.

On the other hand, the medical imaging apparatus 100 may include a variety of devices in addition to the above configuration, and there is no limitation.

Figure 8:
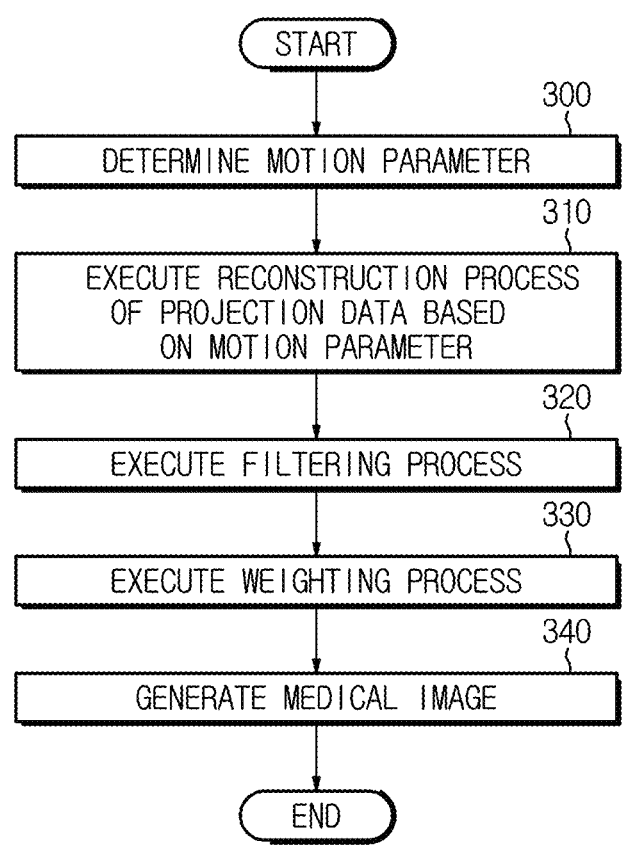
FIG. 8 is a flowchart illustrating a method of generating an image by an image processor according to an embodiment.

FIG. 8 is a flowchart illustrating a method of generating an image by an image processor according to an embodiment.

Referring to FIG. 8, the image processor 140 may determine the motion parameter with respect to the object ob, the X-ray source 110, and the X-ray detector 120 (300).

In detail, the motion parameter may be determined through the image quality metric process as described above. In addition, the motion parameter may be determined by updating an initial parameter value through various techniques processed by the image processor 140.

Meanwhile, the motion parameter may be determined through various methods other than the image quality metric process, and there is no limitation.

The image processor 140 executes the reconstruction process of the projection data based on the determined motion parameter (310).

According to an embodiment, the reconstruction process performed by the image processor 140 may refer to a method of rebinning the collected projection data.

Here, the rebinning may refer to a weaving of collected data, and the rebinning may refer to a process of transforming projection data of the fan-beam or cone-beam geometry into projection data of parallel-beam geometry.

In more detail, the object ob may be scanned through a helical scan method. The X-ray source 110 may scan the object ob in the helical manner, and the image processor 140 may collect the projection data in the form of the fan-beam or cone-beam having a predetermined angle from the X-ray detector 120 at each scan view. The image processor 140 may extract the projection data parallel to each other, having a predetermined length and a predetermined angle, from the projection data collected at each scan view.

A detailed description related to the rebinning will be described later with reference to FIGS. 9 to 13.

The image processor 140 may apply the motion parameter determined at each scan view while performing the rebinning. Conventional rebinning is performed fan-to-parallel without including the motion information of the X-ray source 110 and the X-ray detector 120, but the image processor 140 may convert the views of the X-ray source 110 and the X-ray detector 120 by applying the motion parameter, and may perform the rebinning. Through this, the image quality of the medical image generated by the image processor 140 may be further improved.

The image processor 140 may execute the reconstruction process including the rebinning and then execute a filtering process (320).

The filtering process may execute a method of filling the projection data into regions other than a region in which data exists as a predetermined value to prevent an incorrect corresponding value from being generated, perform data padding, and then execute a ramp filtering process.

The filtering process may include various processes in addition to the ramp filtering process.

The image processor 140 executes a weighting process (330).

The weighting process may refer to a process of applying a new weight function that adds and combines a global weight function Qglobal according to an angle to rebin projection data and a local weight function Qlocal applied to a region in which data exists.

Figure 9:
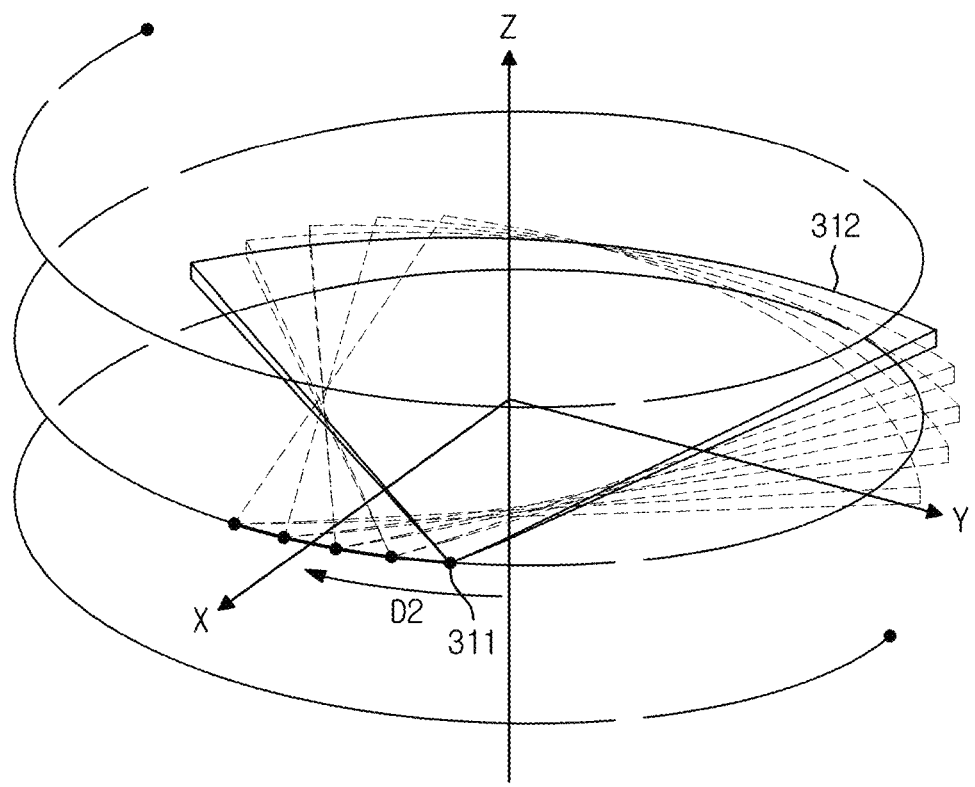
FIGS. 9 and 10 are views for describing a conventional general rebinning method.

Since the conventional weighting process does not include the motion information, the global weight function Qglobal W(q) is simply applied only to a detector row direction (z-axis in FIG. 9). However, the weighting process may distinguish between the region where the projection data exists and the region where the projection data does not exist by applying motion parameters, and may improve the quality of the image by applying a new weight function W(p, q) combining different weight functions with each other. A detailed description thereof will be described later with reference to FIGS. 13 to 15.

The image processor 140 may generate the medical image based on the executed weighting process (340).

Figure 16:
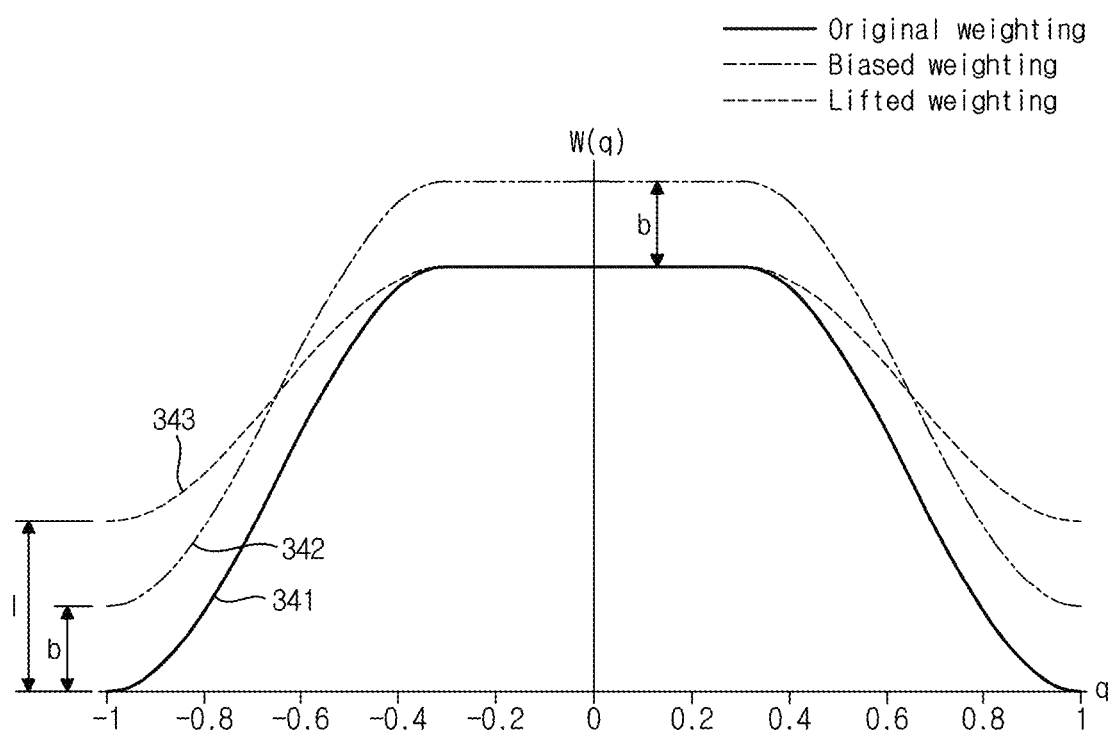
FIG. 16 is a view for describing various embodiments of a weighting process.

That is, the image processor 140 may generate the medical image by performing a back projection process through the new weight function rather than a FDK algorithm used as a conventional back projection process, thereby providing an improved image having reduced artifacts. Specific examples related to the improved image are illustrated in FIG. 16.

Meanwhile, the operation of the image processing may include additional methods in addition to the above-described methods, or may include various processes in addition to the aforementioned processes. As an example, the filtering process may include other filtering in addition to the ramp filtering to prevent a truncation artifact. As another example, the image processing may further proceed with another back projection process after the weighting process.

Figure 10:
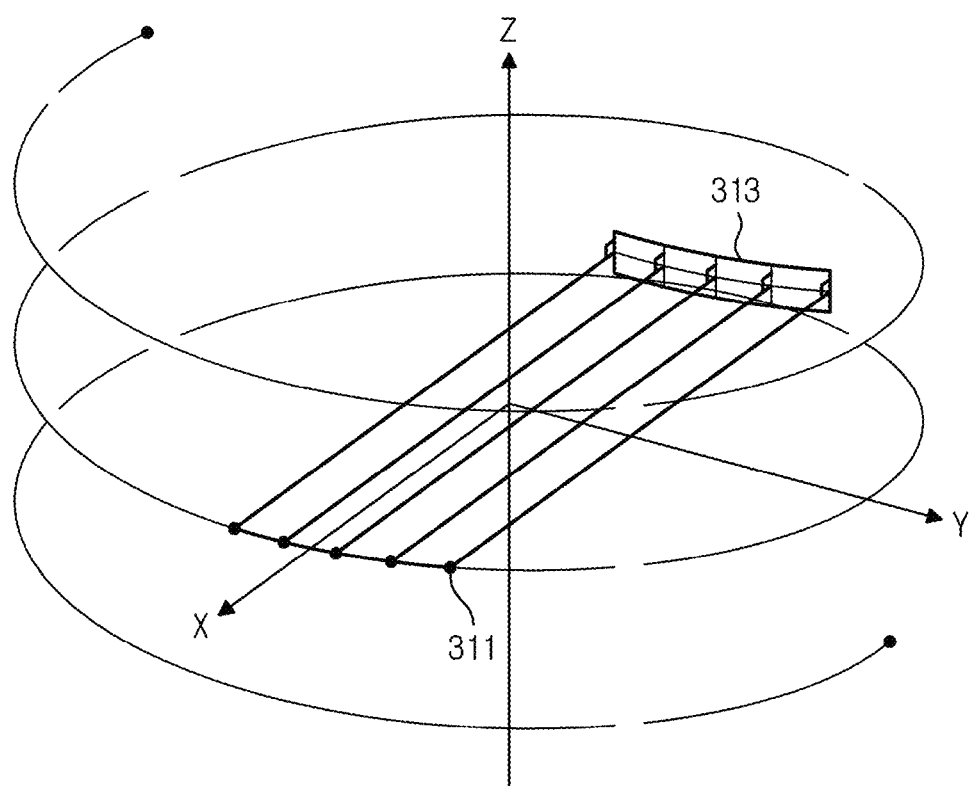

FIGS. 9 and 10 are views for describing a conventional general rebinning method.

In a conventional general rebinning method, as illustrated in FIG. 9 and FIG. 10, the projection data may be collected in a virtual space and the projection data may be converted.

Particularly, in FIG. 9, each of views 311 of the X-ray source 110 may irradiate the fan-beam while moving in a D2 direction along the helical, and the X-ray detector 120 may collect projection data 312 in each of the overlapped regions illustrated in FIG. 9.

Subsequently, in the image reconstruction process, the rebinning may set the projection data parallel to a predetermined angle to generate a rebinning data region 313 as illustrated in FIG. 10, and may proceed with the weighting process in the z-axis (detector row) direction to reduce the artifacts caused by a cone-angle.

In comparison, the image processor 140 may perform the rebinning by applying the motion parameter.

Figure 11:
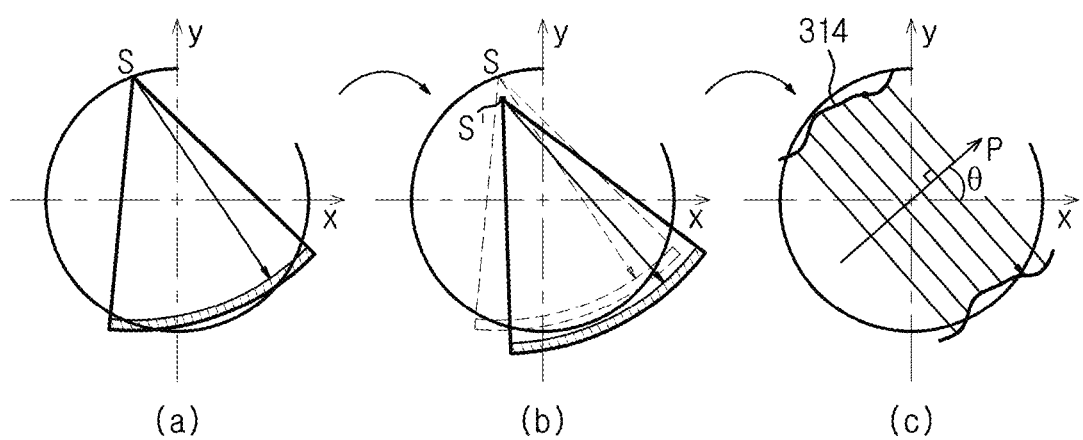
FIG. 11 is a view of a virtual space generated by an image processor viewed from a z-axis according to an embodiment.

FIG. 11 is a view of a virtual space generated by an image processor views in a z-axis according to an embodiment.

In detail, FIG. 11A illustrates fan-beam geometry to which the motion parameter is not applied. The image processor 140 may change an X-ray source S to S' as illustrated in FIG. 11B based on the determined motion parameter.

Thereafter, the image processor 140 may extract a parallel-beam including a predetermined angle Θ from each X-ray source 314 and rebin the projection data through the same.

Figure 12:
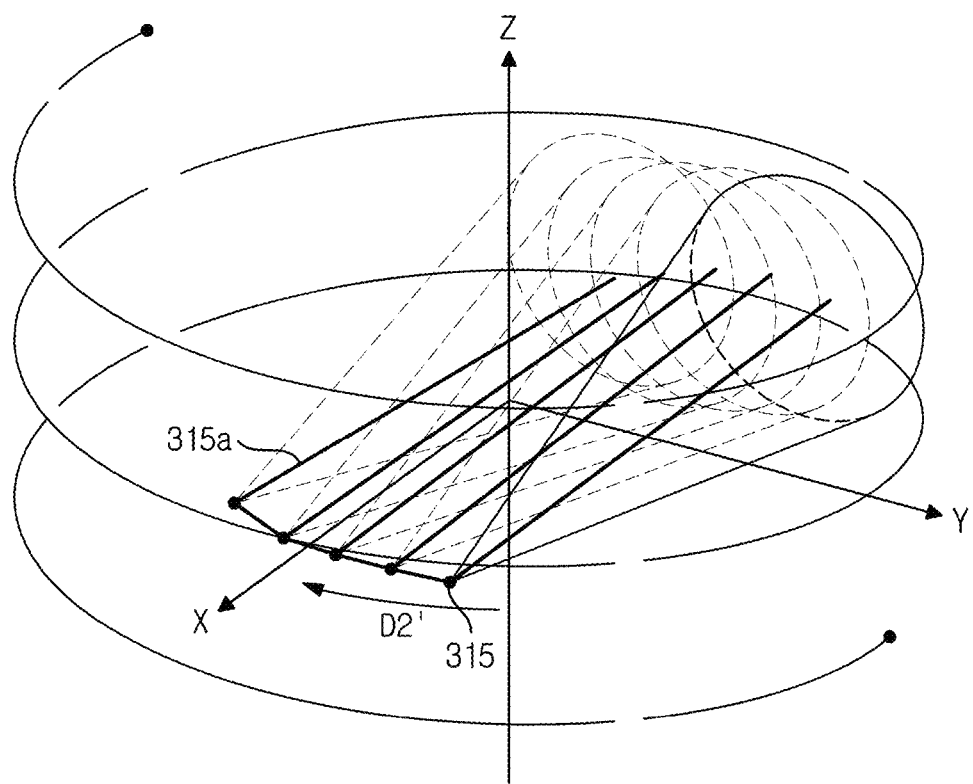
FIGS. 12 and 13 are views for describing cone-beam based rebinning according to an embodiment.
Figure 13:
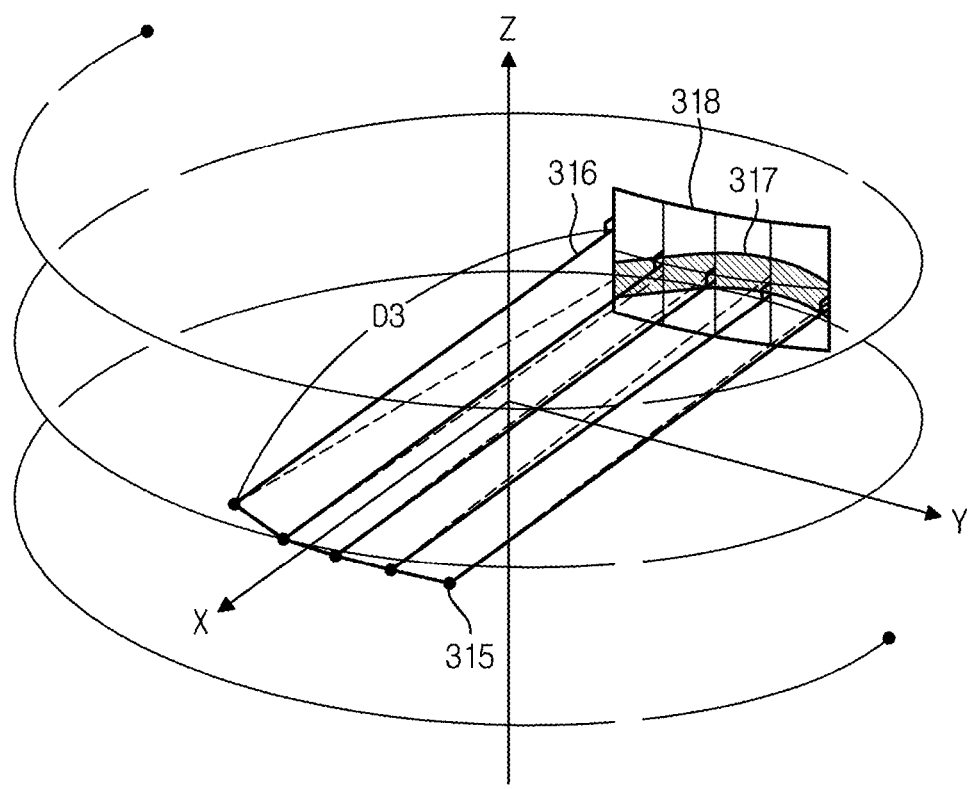

FIGS. 12 and 13 are views for describing cone-beam based rebinning according to an embodiment. The description will be provided together below in order to avoid overlapping description.

The image processor 140 may perform the rebinning based on the fan-beam, but may perform the rebinning based on the cone-beam as illustrated in FIGS. 12 and 13. FIGS. 12 and 13 illustrate that the motion parameter is applied in the z-axis direction.

The image processor 140 may form the cone-beam geometry as illustrated in FIG. 12 based on the raw data and the motion parameters transmitted by the X-ray detector 120. That is, in FIG. 12, each of views 315 corresponding to the X-ray source 110 among the cone-beam geometries may be formed with a movement trajectory D2', which is different from a movement trajectory D2 of the X-ray source 110, by the motion parameter.

Further, a parallel-beam 315a to be formed with a constant reference at each of the views 315 may determine a parallel-beam 316 of FIG. 13 having a constant cone angle and a constant distance D3 after the rebinning is performed. That is, the image processor 140 may determine the parallel-beam 316 and a region 318 perpendicular to the y-axis in the z-axis direction (hereinafter referred to as a 'rebinning detector region').

That is, when the image processor 140 performs the reconstruction process (310 in FIG. 8) through the rebinning, the rebinning detecting region 318 may be extracted. Thereafter, the image processor 140 may perform the filtering process and the weighting process based on the rebinning detecting region 318.

Meanwhile, in FIG. 13, a data present region 317 may correspond to an actual region where the X-ray detector 120 detects the raw data, and may refer to a region in which actual projection data exists among the rebinning detector regions 318.

Generally, when the image is generated through the helical scan, more than two X-rays facing 180 degrees with respect to one voxel may occur. In comparison, the axial scan may generate a maximum of two X-rays facing 180 degrees for one voxel.

An FDK algorithm, which is used in the back projection process and proposed by Feldkamp, Davis, and Kress (FDK), may apply the weighting process (for example, a Parker weighting process) for up to two opposing X-rays, but the FDK algorithm has a problem in that there is no weighting process to be applied when there are more than two X-rays such as in the helical scan.

In order to solve this problem, in the conventional helical scan, when generating one slide image, the scanned projection data was reconstructed by cutting the scanned projection data so that there are two X-rays facing each other. In this method, when a helical pitch increases, a view sample is insufficient and the voxel is dark.

Therefore, the image processor 140 applies the motion parameters and simultaneously applies parallel rebinning to the projection data collected in the helical scan, thereby facilitating the weighting process, which will be described later, and preventing the image from being dark even in a large pitch region.

Figure 14:
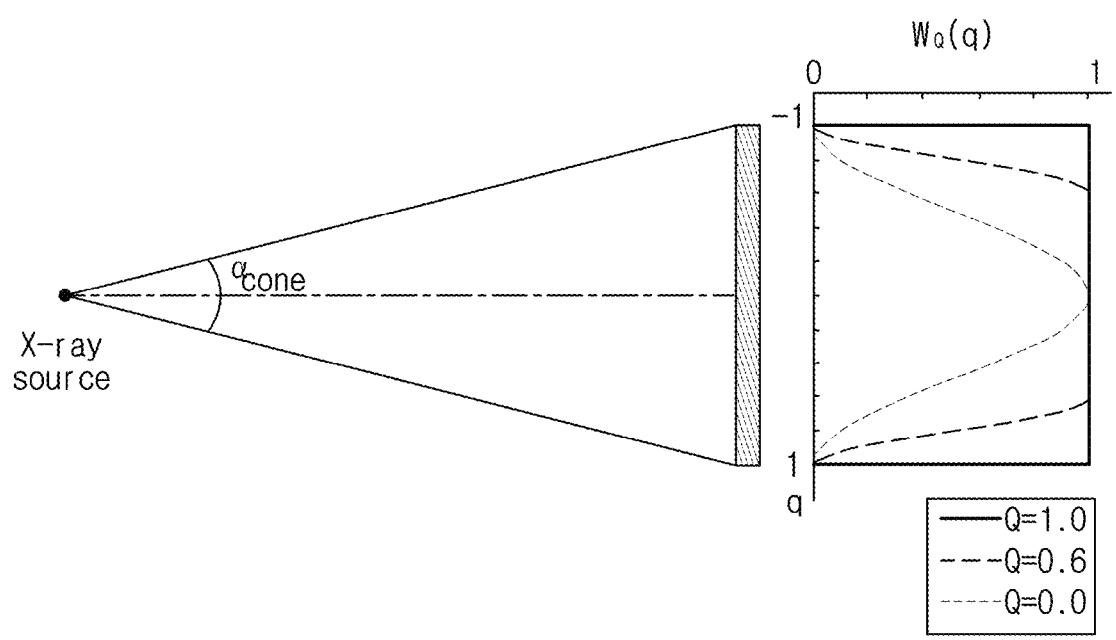
FIGS. 14 and 15 are views for describing a weighting process according to an embodiment.
Figure 15:
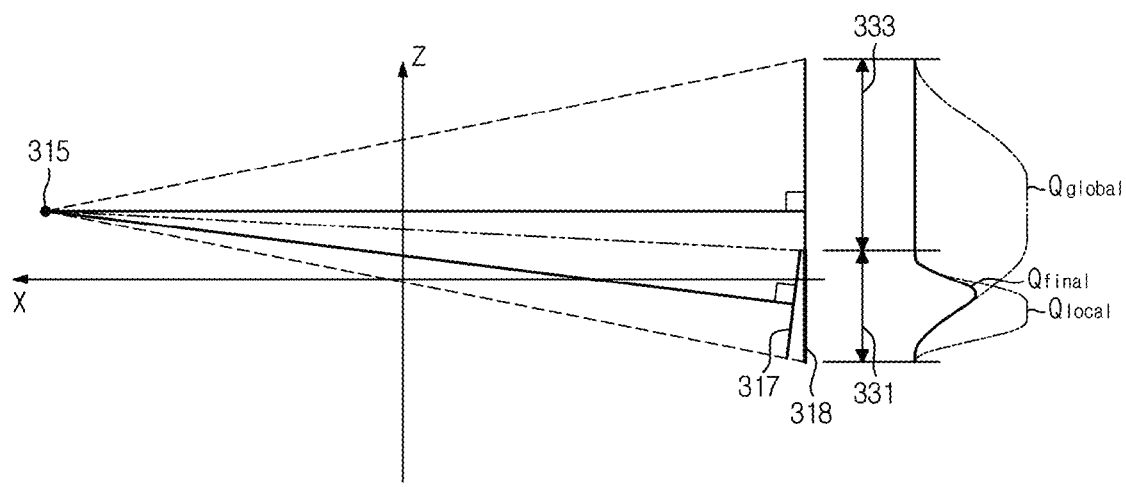

FIGS. 14 and 15 are views for describing a weighting process according to an embodiment. The description will be provided together below in order to avoid overlapping description.

The image processor 140 may perform the rebinning and then perform the filtering process and the weighting process. First, the filtering process may be a method of filling certain data in the z-axis direction with respect to the region in which the data does not exist, that is, the region other than the region 317 in which the data exists in the rebinning detector region 318. As an example, the filtering process may fill the projection data at the end of the region 317 where the data exists with data of the region that does not exist.

After the filtering process, the image processor 140 may execute the process described below.

FIG. 14 is the weighting process applying the conventional weight function WQ(q). Particularly, in the conventional back projection process, the global weight function according to the cone-angle is applied to the projection data to which cone-parallel rebinning is applied. However, in the related art, since the projection data that is not deformed by the motion parameter is used, a batch weight function (hereinafter referred to as the global weight function 'Qglobal') was applied only in the direction of detector row q (z-axis in FIG. 13).

However, the image processor 140 may generate the improved image by applying different weight functions by distinguishing the region 317 and the non-region in which the data exists in the rebinned projection data region based on the motion parameter.

FIG. 15 is a cross-sectional view of the virtual space from the y-axis of FIG. 13. The rebinning detector region 318 rebinned at the view 315 of the X-ray source 110 based on the motion parameter may be classified as a region 331 (hereinafter referred to as a 'first region') in which data actually exists and a region 333 (hereinafter referred to as a 'second region') filled in by the filtering process although the data does not actually exist.

In this case, the weighting process may use a weight function Qfinal generated by combining the weight function applied to the first region 331, that is, the global weight function Qglobal applied to a region in which the local weight function Qlocal and the first region 331 and the second region 333 are combined. For example, the weight function Qfinal may be derived as a result of multiplying the local weight function Qlocal and the global weight function Qglobal.

Accordingly, the image processor 140 may apply the weight process based on the above-described weight function Qfinal to the rebinning detector region in which the data does not exist according to the motion parameter, thereby preventing the possibility of artifacts increasing and generating a clearer image.

FIG. 16 is a view for describing various embodiments of a weighting process.

As described above, the image processor 140 may use the weight function Qfinal combining the local weight function Qlocal and the global weight function Qglobal. Here, the global weight function Qglobal may vary as illustrated in graphs 341 to 343 illustrated in FIG. 16.

In detail, the first graph 341 is a conventional general global weight function Qglobal, and the −1 to a value of 1.

As another example, in the weighting process, the global weight function Qglobal, such as the second graph 342, may be applied. The second graph 342 may not necessarily have the weighting W(q) of the y-axis between 0 and 1, and may have a value between b and b+1. That is, the global weight function Qglobal applied according to the embodiment may be 'biased' than the conventional general global weight function Qglobal.

The global weight function Qglobal, such as the third graph 343, may not necessarily have the weighting W(q) of the y-axis between 0 and 1, and may have a value between c and 1. That is, the global weight function Qglobal applied according to another embodiment may be 'lifted' than the conventional global weight function Qglobal.

On the other hand, the b and c may be changed to various values and is sufficient if set in advance.

Figure 17:
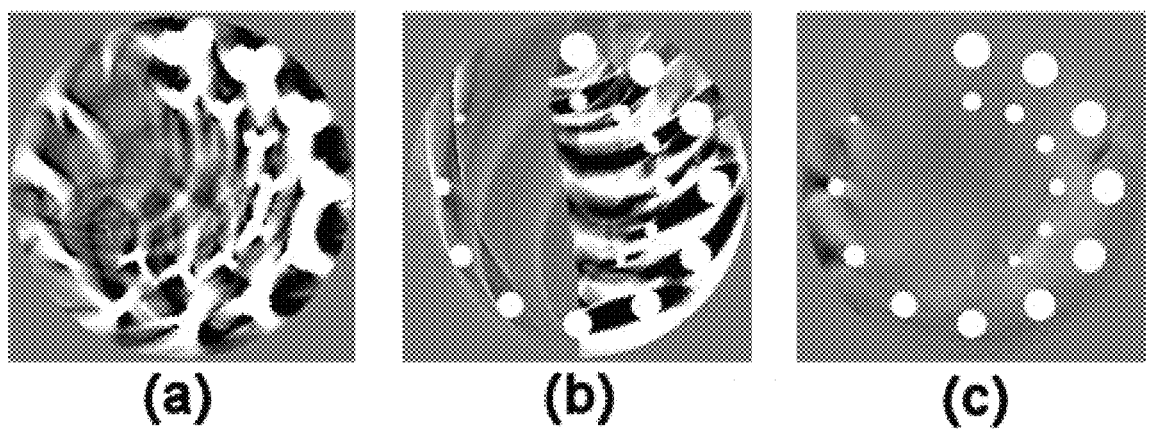
FIG. 17 is a view illustrating a result of image enhancement according to an embodiment.

FIG. 17 is a view illustrating a result of image enhancement according to an embodiment.

FIG. 17A is the medical image to which the reconstruction process and the weighting process are not applied.

FIG. 17B illustrates a result of executing the weighting process to which the global weight function Qglobal is applied although the rebinning is performed. In this case, a right image of FIG. 17B corresponds to the second region 333 and illustrates that the artifact is not improved.

FIG. 17C illustrates that the image is improved after the rebinning, with the image to which the weight function Qfinal generated according to the embodiment is applied.

The workstation, the medical imaging apparatus including the same and a method of controlling the workstation according to the embodiment, may output the medical image having improved image quality with respect to the moving object ob, and in particular, may prevent the phenomenon of darkening in a large pitch region in a three-dimensional (3D) image generated by the helical scan method. It is possible to prevent the phenomena darkening in a region having a large pitch, thus the user of the medical imaging apparatus 100 can accurately diagnose the object ob.

The invention claimed is:

1. A medical imaging apparatus comprising:
an X-ray source configured to irradiate X-rays to an object;
an X-ray detector configured to detect the X-rays radiated from the X-ray source to obtain projection data; and
an image processor configured to reconstruct the projection data based on a motion parameter representing movement of at least one of the object, the X-ray source, and the X-ray detector,
wherein the image processor is configured to rebin the projection data and to generate a medical image by applying a weighting process to the rebinned projection data.

2. The medical imaging apparatus according to claim 1, wherein the image processor is configured to generate a local weight function based on the motion parameter, and to apply the weighting process including the local weight function to the rebinned projection data.

3. The medical imaging apparatus according to claim 2, wherein the image processor is configured to apply the weighting process by combining the local weight function and a preset global weight function.

4. The medical imaging apparatus according to claim 1, wherein the image processor is configured to apply an image quality metric process to determine the motion parameter.

5. The medical imaging apparatus according to claim 1, wherein the image processor is configured to determine the motion parameter by adjusting the reconstructed image based on the projection data.

6. The medical imaging apparatus according to claim 1, wherein the image processor is configured to reconstruct the projection data based on rebinning converting the projection data.

7. The medical imaging apparatus according to claim 6, wherein the rebinning is configured to convert the projection data of fan-beam or cone-beam geometry into projection data of parallel-beam geometry.

8. The medical imaging apparatus according to claim 1, wherein the image processor is configured to apply the weighting process based on the rebinned projection data to which a filtering process is applied.

9. The medical imaging apparatus according to claim 8, wherein the filtering process is configured to apply a ramp filtering process after executing data padding to fill preset projection data.

10. A workstation comprising:
an interface configured to receive a scan command about an object from a user;
a controller configured to control an X-ray source for irradiating X-rays according to the received scan command and an X-ray detector for detecting the irradiated X-rays to obtain projection data; and
an image processor configured to reconstruct the projection data based on a motion parameter representing movement of at least one of the object, the X-ray source, or the X-ray detector,
wherein the image processor is configured to rebin the projection data and to generate a medical image by applying a weighting process to the rebinned projection data.

11. The workstation according to claim 10, wherein the image processor is configured to generate a local weight function based on the motion parameter, and to apply the weighting process including the local weight function to the rebinned projection data.

12. The workstation according to claim 11, wherein the image processor is configured to apply the weighting process by combining the local weight function and a preset global weight function.

13. The workstation according to claim 10, wherein the controller is configured to transmit raw data obtained based on at least one of the scan command, an operation of the X-ray source, or an operation of the X-ray detector to the image processor, and wherein the image processor is configured to preprocess the raw data to obtain the projection data.

14. The workstation according to claim 13, wherein the image processor is configured to generate a sinogram based on the projection data, and to reconstruct the projection data based on the sinogram.

15. A method of controlling a workstation comprising:
receiving a scan command about an object from a user;
controlling an X-ray source for irradiating X-rays according to the received scan command and an X-ray detector for detecting the irradiated X-rays to obtain projection data; and
generating a medical image based on a motion parameter representing movement of at least one of the object, the X-ray source, or the X-ray detector.

* * * * *